(12) United States Patent
Goetsch et al.

(10) Patent No.: US 6,268,536 B1
(45) Date of Patent: *Jul. 31, 2001

(54) CONVERSION OF AMMONIUM PICRATE TO VARIOUS USEFUL CHEMICAL PRODUCTS

(76) Inventors: Duane A. Goetsch, 14399 Raven St., NW., Andover, MN (US) 55304; Kym B. Arcuri, 11921 S. Forest Pl., Jenks, OK (US) 74037

( * ) Notice: Subject to any disclaimer, the term of this patent is extended or adjusted under 35 U.S.C. 154(b) by 0 days.

This patent is subject to a terminal disclaimer.

(21) Appl. No.: 09/454,760

(22) Filed: Dec. 6, 1999

Related U.S. Application Data

(63) Continuation-in-part of application No. 09/149,938, filed on Sep. 9, 1998, now Pat. No. 5,998,676.

(51) Int. Cl.⁷ .................................................. C07C 209/00
(52) U.S. Cl. ........................... 564/418; 564/421; 564/422
(58) Field of Search ...................................... 564/418, 421, 564/422

(56) References Cited

U.S. PATENT DOCUMENTS

| 4,661,179 | 4/1987 | Hunter et al. | 149/124 |
|---|---|---|---|
| 5,530,175 | 6/1996 | Johnson et al. | 588/203 |
| 5,582,119 | 12/1996 | Barkdoll | 110/346 |
| 5,990,354 | * 11/1999 | Goetsch | 564/421 |

* cited by examiner

*Primary Examiner*—Michael L. Shippen

(57) ABSTRACT

A process for the conversion of a picrate salt, preferably ammonium pricrate, to picric acid by acidifying the picrate salt in a two phase liquid system. One phase is an aqueous phase which contains an acid which is effective for acidifying ammonium picrate to picric acid and the other phase is an organic solvent phase in which the picric acid is soluble.

10 Claims, No Drawings

CONVERSION OF AMMONIUM PICRATE TO VARIOUS USEFUL CHEMICAL PRODUCTS

CROSS-REFERENCE TO RELATED APPLICATIONS

This application is a continuation-in-part of U.S. application Ser. No. 09/149,938 filed Sep. 9, 1998, now U.S. Pat. No. 5,998,676.

FIELD OF THE INVENTION

The present invention relates to a process for the conversion of a picrate salt, preferably ammonium pricrate, to useful chemical products, such as triaminophenol, triaminobenzene, picramic acid, and salts of picramic acid.

BACKGROUND OF THE INVENTION

There is a need to destroy, or reclaim, explosive materials as part of the demilitarization effort. Procedures conventionally used to demilitarize conventional munitions include incineration of reclaimed explosives and open burning or detonation. Some explosive materials, such as ammonium picrate, also known as Explosive "ID", are of high enough purity to be economically suitable for conversion to higher value chemicals.

The destruction of nitrogen-containing explosives has been the subject of various disclosures. For example, German patent publication DE 413147-A1 discloses the hydrogenation of nitro-aromatic explosives in the presence of an alcohol solvent, hydrogen, and a catalyst at a temperature of about 40° C. to 100° C. Also, U.S. Pat. No. 4,661,179 discloses a process for destroying waste explosives containing nitro, nitrate, or nitroamino groups by hydrogenation. Further, U.S. Pat. No. 5,582,119 teaches a method for destroying explosive waste, such as those containing ammonium picrate, by use of a vessel containing a hot granular bed of sand to ignite the waste and to dampen explosive forces generated by its ignition.

U.S. Pat. No. 5,530,175 discloses a process for converting ammonium picrate to oxygenated products, particularly hydroquinone or cyclohexanediol and ammonia, by hydrogenation over a supported Group VIII metal catalyst. The ammonium picrate is dissolved in a suitable solvent, then hydrogenated at a temperature of about 25° to 250° C., followed by separation of the resulting products and ammonia.

It is also known in the art that ammonium picrate can be converted to picric acid by acidification with a strong acid, at an appropriate pH and acid/salt ratio in an aqueous system. The concentration of picric acid must be kept relatively low because as the concentration of picric acid increases, its rate of formation decreases.

While there exists methods for converting ammonium picrate to more useful products, such as to picric acid, there remains a need for processes that can do this conversion more efficiently and economically.

SUMMARY OF THE INVENTION

In accordance with the present invention there is provided a process for converting ammonium picrate to triaminophenol which process comprises:

a) reacting the ammonium picrate with a strong inorganic acid in an aqueous medium, thereby producing picric acid and the ammonium salt of the strong acid;

b) separating said picric acid, from the ammonium salt, by dissolving it in an organic solvent; and c) hydrogenating said picric acid with a hydrogenation catalyst at suitable conditions thereby converting the picric acid to picramic acid, triaminophenol, or both.

In a preferred embodiment of the present invention the triaminophenol is treated by removing the hydroxyl group from said triaminophenol by reacting it with a hydrogen-containing treat gas in the presence of a hydrotreating catalyst, at suitable hydrotreating conditions, thereby converting said triaminophenol to triaminobenzene.

In another preferred embodiment of the present invention the hydrotreating catalyst used in steps c) and d) is selected from those comprised of a Group VIII metal selected from Ni and Co, and a Group IV metal selected from Mo and W, on an inorganic refractory support.

DETAILED DESCRIPTION OF THE INVENTION

The acidification of ammonium picrate to picric aid is known in the art and is generally preformed in an aqueous medium wherein ammonium picrate is reacted with a suitable acid, typically a strong acid such as a mineral acid, at an effective pH and within a suitable acid/salt ratio. As the reaction proceeds, the concentration of picric acid in the aqueous phase increases to a level that will significantly slow the acidification reaction, thus severely affecting the economics of the process. Consequently, it is necessary to maintain a relatively low concentration of picric acid in the aqueous phase in order to maintain acceptable acidification reaction rates. This is not generally acceptable because maintaining a low concentration of picric acid results in a substantially less efficient process. Thus, it would be highly desirable to be able to produce picric acid from ammonium prcrate so that the picric acid produced would not adversely effect the rate of picric acid formation.

The process of the present invention solves the above problem by providing a two phase system. Both phases are liquid, wherein one phase is an aqueous phase in which the acidification reaction takes place, and the other is an organic phase in which the picric acid is soluble. Thus, the acidification reaction is not adversely affected because as the picric acid is formed it dissolves into the organic phase, thereby keeping the concentration of picric acid in the aqueous phase relatively low. As previously mentioned the organic phase is comprised of an organic solvent in which picric acid is substantially soluble. Organic solvents which are suitable for use in the present invention are those which have a relatively low vapor pressure (boiling point), and in which the picric acid will readily dissolve, and which have substantially negligible aqueous solubility. In other words, the organic solvent is one which has a relatively low partition coefficient with respect to the aqueous phase but in which the picrate acid has a relatively high partition coefficient. That is, the picric acid will strongly favor the organic phase over the aqueous phase. Preferred solvents include toluene and xylene, as well as other suitable organic materials which can be used. Further, the use of an organic solvent increases the efficiency of the acidification process since a smaller acid-ammonium picrate contact volume for producing a given amount of picric acid. The solubility of picric acid in many commercially available organic solvents (i.e. toluene) is 5 to 25 times higher than its solubility in water. The use of an organic solvent with a low aqueous solubility and high vapor pressure simplifies the picric acid recovery step. The insoluble organic phase containing the picric acid product is separated from the aqueous phase using conventional state of the art oil-water separation technology.

Acids suitable for use in the practice of the present invention are those acids which are strong enough to effectively acidify ammounium picrate to picric acid in an aqueous medium. A strong acid is needed in order to provide the hydronium ions necessary to produce picric acid. The specific acid and concentration level depends upon several technical issues which ultimately affect process economics. The amount of acid used will depend upon such things as the equilibrium of the acidification as well as the impact on the solubility of the resulting acid and salts. Non-limiting examples of such acids are the mineral acids selected from the group consisting of sulfuric acid, nitric acid, and chloric acid. A preferred acid would be one which results in an ammonium salt product that has commercial value. Thus, the most preferred acid, from a commercial point of view is nitric acid because the resulting ammonium nitrate could be used for agricultural purposes.

The instant process can be practiced in any suitable manner as long as the two liquid phases are present during the formation of picric acid and before the concentration of picric acid reaches unacceptable high levels in the aqueous phase. For example, the strong acid can be added to an aqueous solution of ammonium picrate, thereby resulting in an acidification reaction wherein picric acid is produced, as well as an ammonium salt. The amount of acid used will depend on such things as the level of pH needed to ensure relatively high picrate acidification. Typically the pH will be less than about 5, such as between about 3 and 5, although a lower pH may also be used. The organic solvent is then added before the concentration of picric acid increases to a level that would significantly decrease the rate of acidification. The concentration of ammonium picrate in water can vary depending on such things as the desired quality of the product picric acid. It is preferred that less than about 20 wt. %, more preferably less than about 15 wt. % of ammonium picrate be present, based on the total weight of ammonium picrate and water. Of course, the temperature of the aqueous solution will play a role in the potential concentration of ammonium picrate. For example, the solubility of ammonium picrate will increase with increasing temperatures. The organic phase, containing the picric acid, can be drawn off and the picric acid separated from the organic solvent by conventional separation techniques, such as by flashing the solvent and recovering the remaining picric acid. The organic solvent can then be recycled.

As the reaction proceeds, the concentration of salt in the aqueous phase will increase to unacceptable levels. When this happens, a fraction of the salt-containing aqueous solution can be withdrawn and the salt recovered by conventional techniques, such as in a crystallizer vessel. This will help ensure that the level of salt be maintained at level that will not adversely affect the acidification reaction.

Another process scheme can be envisioned wherein a mixture of water and organic solvent are provided into which is added ammonium picrate and a strong acid. The mixture is then thoroughly stirred and the organic phase containing the picric acid drawn off and passed to a separation step where the picric acid is separated from the solvent by conventional means. The organic solvent can be recycled.

A solvent wash may be employed with any of the process options to achieve a higher product purity and avoid the use of excess acid or water. The limited solubility available thus far indicates that picric acid has a relatively high solubility in ethyl alcohol compared to ammonium picrate (7.5 versus 0.35 gms/100 gms water when no acid is present). Consequently, an alcohol wash may be effective in removing trace acid, water, and/or dissolved ammonium salt.

The picric acid, in the organic solvent, from the above step is passed to a hydrogenation zone where it is catalytically hydrogenated with a hydrogen-containing treat gas, preferably hydrogen. Suitable conditions are used to convert the nitro groups of picric acid to amino groups, thereby producing the corresponding triaminophenols. Picric acid from other sources can also be processed in accordance with the present invention, either as a separate feedstream, or blended with the picric acid obtained in the above acidification reaction. Any suitable hydrogenation catalyst may be used for this step. Non-limiting examples of such hydrogenation catalysts include those containing Group VIII metals, such as Pt, Pd, Rh, Ni, and Co, and mixtures thereof The Ni may be in the form of Raney Ni. Although other hydrogenation catalysts may be used, the noble metals, Pt and Pd are preferred, more preferred is Pd. The catalytic metals could be used alone in finely divided particulate form, but preferably they are supported on suitable support materials, preferably refractory inorganic support materials, such a carbon, alumina, silica, silica-alumina, titania, zeolitic materials, and the like. In preferred embodiments of the present invention the metal is deposited onto the support by conventional catalyst preparation techniques in an amount between about 0.1 to 5 wt. %, preferably from about 0.3 to 4 wt. %, and more preferably from about 0.3 to 3 wt. %. Conventional techniques for depositing the metal onto the support material include impregnation of the support with a solution of a noble metal compound followed by heating to decompose the noble metal compound, leaving a finely dispersed metal on the support. Other suitable methods, such a co-precipitation of the metal compound and the support material from solution can also be used. The hydrogenation reaction will typically be conducted at temperatures from about 25° C. to about 150° C., preferably from about 50° C. to about 100° C. The reaction will generally be carried out with a positive pressure, preferably between 5 to 500 psig (69 to 6,900 kPa gauge), preferably about 20 to 200 psig (689 to 4,826 kPa).

The hydrogenation catalyst may be treated with a small amount of hydrogen sulfide to minimize metal cracking and/or hydrogenolysis reactions. Metal cracking results in unstable species that form carbonaceous deposits and loss of catalytic activity. Similarly, a small amount of CO can be added to the hydrogen stream to inhibit these undesirable reactions.

Hydrogen will be maintained at mole ratios of about 2/1 to 50/1 relative to the picric acid reacted to make triaminophenol. The preferred system can employ recycle of the hydrogen containing gas. The use of recycle hydrogen can lead to enhanced process efficiency in terms of operating costs. Under the reaction temperatures and pressures the picric acid containing solvent will be liquid and the hydrogen a gas, so that a two-phase (gas/liquid) mixture will be passed over the supported catalyst at a liquid hourly space velocity based on the picric acid of about 0.1 to 10 $hr^{-1}$, preferably between about 0.5 and 1 $hr^{-1}$. The preferred liquid hourly space velocity will depend upon the activity of the catalyst and the reaction temperature.

The triaminophenol produced from the hydrogenation of picric acid is passed to a first hydrotreating zone where it is reacted with a hydrogen-containing treat gas in the presence of a hydrotreating catalyst at conditions which are effective to remove the hydroxyl group from the triaminophenol, thereby producing triaminobenzene. The term "hydrotreating" as used herein refers to processes wherein a hydrogen-containing treat gas is used in the presence of a suitable catalyst which is primarily active for the removal of heteroatoms, such as sulfur, oxygen, and nitrogen, with some hydrogenation of aromatics. Suitable hydrotreating catalysts for use in the present invention are any conventional hydrotreating catalyst, particularly those which are comprised of at least one Group VIII metal, preferably Fe, Co and Ni, more preferably Co and/or Ni, and most preferably Co; and at least one Group IV metal, preferably Mo and W, more preferably Mo, on an inorganic refractory support material, preferably alumina. Other suitable hydrotreating catalysts include zeolitic catalysts, as well as noble metal catalysts where the noble metal is selected from Pd and Pt. The Group VIII metal is typically present in an amount ranging from about 2 to 20 wt. %, preferably from about 4 to 12%. The Group IV metal will typically be present in an amount ranging from about 5 to 50 wt. %, preferably from about 10 to 40 wt. %, and more preferably from about 20 to 30 wt. %. All metals weight percents are on support. By "on support" we mean that the percents are based on the weight of the support. For example, if the support were to weigh 100 g. then 20 wt. % Group VIII metal would mean that 20 g. of Group VIII metal was on the support. Typical hydrotreating temperatures range from about 150° C. to about 400° C., preferably from about 250° C. to about 350° C., with pressures from about 50 psig to about 2,000 psig, preferably from about 200 psig to about 800 psig.

The product from this first hydrotreating zone is triaminobenzene which can be passed to a second hydrotreating zone, using a catalyst selected from those described for the first hydrotreating zone, and under conditions which will be effective for the removal of one or more amino groups. It is within the scope of the present invention that only one hydrotreating zone be present wherein both the conversion of triaminophenol to triaminobenzene and the conversion of triaminobenzene to phenylenediamines simultaneously occur.

It is also within the scope of this invention to convert picric acid to picraric acid by hydrogenating at least one of the ortho $NO_2$ groups of picric acid to an $NH_2$ group. The hydrogenation is accomplished by treating the picric acid under hydrogenation conditions with a hydrogenation catalyst. Selective hydrogenation of picric acid can be accomplished by properly adjusting the feed ratios of hydrogen to picric acid, the catalyst, and the temperature and pressure of reaction. By judiciously choosing these conditions one is able to selectively hydrogenate one, two, or all three of the $NO_2$ groups to $NH_2$ groups. The resulting picramic acid can then be converted to its corresponding salt, for example sodium picramate by reacting picric acid with NaOH.

What is claimed is:
1. A process for converting ammonium picrate to picramic acid, triaminophenol, or both which process comprises:
   a) reacting the ammonium picrate with a strong inorganic acid in an aqueous medium, thereby producing picric acid and the ammonium salt of the strong acid;
   b) separating said picric acid, from the ammonium salt, by dissolving said picric acid in an organic solvent; and
   c) hydrogenating said picric acid with a hydrogenation catalyst at suitable conditions thereby converting the picric acid to picramic acid, triaminophenol, or both.
2. The process of claim 1 wherein the triaminophenol is treated by removing the hydroxyl group from said triaminophenol by reacting it with a hydrogen-containing treat gas in the presence of a hydrotreating catalyst, at suitable hydrotreating conditions, thereby converting said triaminophenol to triaminobenzene.
3. The process of claim 1 wherein the reactor used for the hydrogenation of the picric acid is a slurry reactor which is effective for dissipating the heat generated during the hydrogenation reaction.
4. The process of claim 1 wherein the hydrogenation catalyst is comprised of transition metal on an inorganic refractory support.
5. The process of claim 4 wherein the transition metal is a Group VIII metal.
6. The process of claim 2 wherein the hydrotreating catalyst is selected from those comprised of at least one Group VIII metal selected from Ni and Co, and at least one Group IV metal selected from Mo and W, on an inorganic refractory support.
7. The process of claim 1 wherein the strong acid is selected from the group consisting of nitric acid, sulfuric acid, and hydrochloric acid.
8. The process of claim 4 wherein the hydrogenation catalyst was pretreated with an effective amount of sulfur in the presence of CO.
9. The process of claim 1 wherein the triaminophenol is treated by removing a hydroxyl group and an amino group from said triaminophenol by reacting it with a hydrogen-containing treat gas in the presence of a hydrotreating catalyst, at suitable hydrotreating conditions, thereby converting said triaminophenol to the corresponding phenylenediamine.
10. The process of claim 1 wherein the triaminobenzene is further treated by removing an amino group from said triaminophenol by reacting it with a hydrogen-containing treat gas in the presence of a hydrotreating catalyst, at suitable hydrotreating conditions, thereby converting said triaminobenzene to the corresponding phenylenediamine.

* * * * *